(12) United States Patent
Kawakami et al.

(10) Patent No.: US 7,776,019 B2
(45) Date of Patent: Aug. 17, 2010

(54) BREAST MILK ABSORBENT PAD

(75) Inventors: Hikari Kawakami, Kagawa-ken (JP); Michiyo Fujikawa, Kagawa-ken (JP)

(73) Assignee: Uni-Charm Corporation, Ehime (JP)

(*) Notice: Subject to any disclaimer, the term of this patent is extended or adjusted under 35 U.S.C. 154(b) by 214 days.

(21) Appl. No.: 12/034,026

(22) Filed: Feb. 20, 2008

(65) Prior Publication Data

US 2008/0294136 A1 Nov. 27, 2008

(30) Foreign Application Priority Data

Feb. 20, 2007 (JP) ............................. 2007-039809

(51) Int. Cl.
*A61F 13/45* (2006.01)
*A61F 13/15* (2006.01)

(52) U.S. Cl. .................. 604/385.07; 604/346

(58) Field of Classification Search ............... 604/346, 604/348–349, 385.07; 450/37, 39, 65–70, 450/90–92
See application file for complete search history.

(56) References Cited

U.S. PATENT DOCUMENTS

| | | | | | |
|---|---|---|---|---|---|
| 2,420,575 | A | * | 5/1947 | Treadwell | 450/39 |
| 2,498,487 | A | * | 2/1950 | Elias | 450/78 |
| 2,505,720 | A | * | 4/1950 | Cooper-Smith et al. | 128/889 |
| 2,707,281 | A | * | 5/1955 | Barth | 450/39 |
| 3,772,899 | A | * | 11/1973 | Novi | 66/176 |
| 4,390,024 | A | * | 6/1983 | Williams | 450/36 |
| 5,269,720 | A | * | 12/1993 | Moretz et al. | 450/37 |
| 5,385,502 | A | * | 1/1995 | Moretz et al. | 450/93 |
| 5,439,409 | A | * | 8/1995 | McCracken et al. | 450/31 |
| 5,690,536 | A | * | 11/1997 | Madden et al. | 450/37 |
| 5,850,745 | A | * | 12/1998 | Albright | 66/176 |
| 5,858,014 | A | * | 1/1999 | Kepes et al. | 604/387 |
| 5,862,527 | A | * | 1/1999 | Trevino | 2/406 |
| 6,015,331 | A | * | 1/2000 | Ioakim | 450/37 |
| 6,036,577 | A | * | 3/2000 | Coburn | 450/57 |
| D433,786 | S | * | 11/2000 | Gladstone | D2/708 |
| 6,257,951 | B1 | * | 7/2001 | DeMarco | 450/55 |
| 6,257,952 | B1 | * | 7/2001 | Valentin | 450/81 |
| 6,364,741 | B1 | * | 4/2002 | Ferguson | 450/57 |
| 6,837,771 | B2 | * | 1/2005 | Falla | 450/39 |
| 6,863,589 | B2 | * | 3/2005 | Cano | 450/65 |
| 2006/0057937 | A1 | * | 3/2006 | Bowler | 450/61 |
| 2007/0083180 | A1 | * | 4/2007 | Sakaguchi et al. | 604/385.07 |
| 2007/0287977 | A1 | * | 12/2007 | Fujikawa et al. | 604/385.07 |

(Continued)

FOREIGN PATENT DOCUMENTS

FR 2753607 A1 * 3/1998

(Continued)

OTHER PUBLICATIONS

Definitions of "compartment", "concave" and "round", Merriam-Webster OnLine.*

*Primary Examiner*—Karin M Reichle
(74) *Attorney, Agent, or Firm*—Brinks Hofer Gilson & Lione (57) ABSTRACT

A breast milk absorbent pad which includes first and second sections adapted to cover respective breasts and a third section extending between these first and second sections wherein at least one of upper and lower edges of the third section is concavely curved toward a transverse axis of the breast milk absorbent pad.

9 Claims, 4 Drawing Sheets

U.S. PATENT DOCUMENTS

| | | | |
|---|---|---|---|
| 2007/0287978 A1* | 12/2007 | Fujikawa et al. | 604/385.07 |
| 2008/0026676 A1* | 1/2008 | Rothman et al. | 450/36 |
| 2008/0287036 A1* | 11/2008 | McGuire | 450/23 |
| 2009/0131900 A1* | 5/2009 | Tsutsui et al. | 604/385.07 |
| 2009/0203295 A1* | 8/2009 | Kassel | 450/37 |
| 2009/0265830 A1* | 10/2009 | Hendrickson | 2/104 |
| 2009/0265831 A1* | 10/2009 | Hendrickson | 2/104 |

FOREIGN PATENT DOCUMENTS

| | | | |
|---|---|---|---|
| GB | 2377618 A | * | 1/2003 |
| JP | 200-178805 | | 6/2000 |
| JP | 2004-332178 | | 11/2004 |
| JP | 2005126836 A | * | 5/2005 |
| WO | WO 02080710 A1 | * | 10/2002 |
| WO | WO 2004030478 A1 | * | 4/2004 |

* cited by examiner

BREAST MILK ABSORBENT PAD

BACKGROUND OF THE INVENTION

The present invention relates generally to a breast milk absorbent pad adapted to be inserted between a brassiere and breasts.

There have already been proposed breast milk absorbent pads comprising a liquid-pervious sheet facing the wearer's skin, a liquid-impervious sheet facing away from the wearer's skin and a body fluid absorbent core. For example, Japanese Unexamined Patent Application Publication No. 2000-178805 (Reference 1) discloses paired breast milk absorbent pads each comprising a basic pad consisting of an absorbent unit for absorbing body fluids and a water-proof member affixed to the outer side of the absorbent unit. Stretchable/contractible members provided along upper and lower edges of the absorbent unit provide contractible forces so that the basic pads may develop three-dimensional shapes adapted to shapes of the respective breasts. Japanese Unexamined Patent Application Publication No. 2004-332178 (Reference 2) discloses a breast milk absorbent pad of so-called long from side to side type comprising a film layer and a water-absorbent layer bonded to each other so that this continuous laminated sheet may be folded to cover both breasts.

During a nursing period, breast milk is constantly secreted and consequentially an amount of breast milk accumulated in a lacteal gland often overspills from nipples. Furthermore, breast milk is also released from the nipple of the breast when the feeding of a baby is not taking place due to inevitable physiological phenomena. With the widely used paired breast milk absorbent pads in which the individual pads are separated from each other as disclosed in Reference 1, the amount of released breast milk may often exceed the absorption capacity of the pad and seep through the pad.

During a nursing period, a mother sometimes lies still alongside her baby to breast-feed the baby for example when the baby cries him-or herself to sleep at bed time. In such situation, a coupler means of the brassiere has previously been released and therefore its retaining ability for a pad is no more present. As a result, the higher breast that is not being used for breast-feeding and the pad are subjected to a downward directed force such as the weight of the breast that is being used for breast-feeding. However, the breast milk absorbent pad fastened to the brassiere or clothes does not droop together with the breast and this breast alone droops until it is exposed from the pad. The amount of breast milk released from the nipple of this breast may flow down along the wearer's skin and often the clothes may be contaminated with such breast milk.

Figure 5:
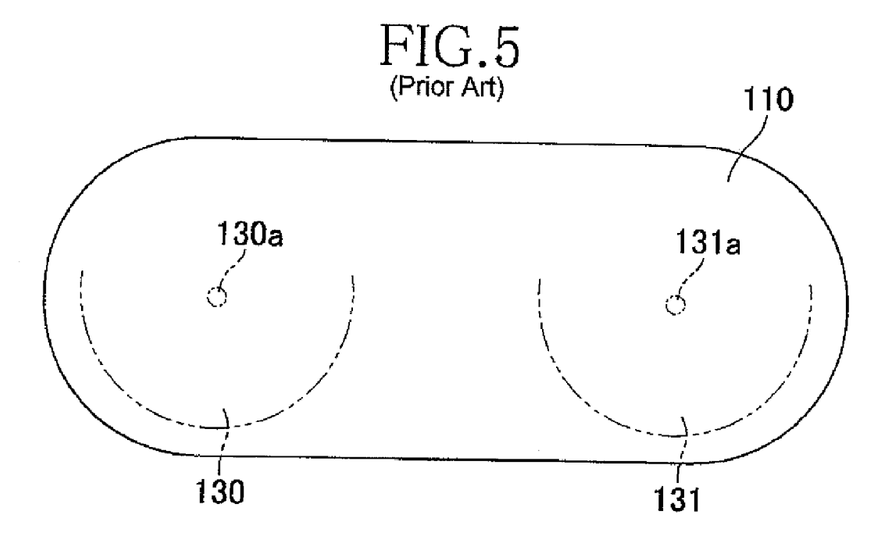
FIG. 5 is a plan view exemplarily showing the breast milk absorbent pad of prior art.

According to the breast milk absorbent pad disclosed in Reference 2, both breasts 130, 131 can be covered with the single pad 110 and a chest region defined between the breast 130 and the breast 131 is also provided with the absorbent means as will be apparent from FIG. 5 of the accompanying drawings. In this way, a total area of the absorbent means is larger than that of individual pads that are separated from each other by the chest region and overall absorption capacity also is higher than that of the individual pads. Furthermore, any anxiety that breast milk flowing downward might leak out along the chest region defined between the breasts 130, 131 can be effectively alleviated.

However, the breast milk absorbent pad 110 has a transversely longer elliptical shape having a transverse dimension substantially corresponding to a shoulder width of the wearer and has no means in the chest region defined between the breasts to distinguish the respective breasts from each other. In other words, this pad lacks a three-dimensional shape adapted to the respective breasts. As a result, the breasts 130, 131 are not stably held within the breast milk absorbent pad 110 and any significant movement and/or posture change of the wearer may cause positions of the respective breasts 130, 131 to get out of proper positions vertically and/or laterally relative to the breast milk absorbent pad 110. In particular when breast-feeding is carried out when the wearer is lying on her side, the unused breast may droop downward (i.e., toward the breast being used for breast-feeding). The nipples 130a, 131a are no more in contact with the inner surface of the breast milk absorbent pad 110 and the amount of breast milk released from these nipples cannot be absorbed by the pad 110. Eventually such amount of breast milk may flow down along the wearer's body and contaminate the clothes.

SUMMARY OF THE INVENTION

An object of the present invention is to solve the problems as have been described above and the other objects of the present invention will be understood from the description given hereunder.

According to the present invention, there is provided a breast milk absorbent pad having a longitudinal axis, a transverse axis, an inner side facing the pad wearer's skin, an outer side facing away from the pad wearer's skin, and upper and lower edges opposed to each other in a direction defined by the longitudinal axis and extending in a direction defined by the transverse axis, the breast milk absorbent pad comprising a body fluid absorbent layer comprised of a body fluid pervious inner sheet lying on the inner side facing the pad wearer's skin and a body fluid absorbent panel, and a body fluid leak-barrier outer sheet lying on the outer side facing away from the pad wearer's skin, wherein the breast milk absorbent pad is compartmented in first and second sections symmetric about the longitudinal axis and a third section extending continuously between the first and second sections.

The present invention further comprises at least one of the upper and lower edges in said third section is shaped to be concavely curved toward the transverse axis.

The present invention may be exploited also in preferred embodiments as follows:

An embodiment wherein the upper and lower edges in at least one of the first and second sections are provided with elastically stretchable/contractible members extending in the direction defined by the transverse axis and attached under tension to these upper and lower edges.

An embodiment wherein the concavely curved edge in the third section described a circular arc.

An embodiment wherein the upper and lower edges are defined by upper and lower flaps extending outward from upper and lower edges of the body fluid absorbent panel in the direction defined by the longitudinal axis, the upper and lower flaps are formed by edges of the inner sheet extending outward beyond the upper and lower edges of the body fluid absorbent panel and edges of the outer sheet extending outward beyond the upper and lower edges of the body fluid absorbent panel and wherein the elastically stretchable/contractible members comprise a first par of elastically stretchable/contractible members attached under tension to the outer sheet along its outermost edges and a second pair of elastically stretchable/contractible members attached under tension to the outer sheet along the upper and lower edges of the body fluid absorbent panel.

An embodiment wherein the upper and lower edges of the body fluid absorbent panel extending in the vicinity of the upper and lower edges concavely curved toward the transverse axis, respectively, in the third section do not intersect with the transverse axis.

An embodiment wherein the one of the upper and lower edges opposed to the other edge concavely curved toward the transverse axis in the third section is linear and an elastically stretchable/contractible member continuously extends along said first section, the third section and the second section.

An embodiment wherein a dimension of the body fluid absorbent panel in the third section as measured in the direction defined by the longitudinal axis is in a range of 0.4 to 0.8 times a dimension of the body fluid absorbent panel in the first and second sections as measured in the direction defined by the longitudinal direction.

An embodiment wherein a stiffness of the body fluid absorbent panel as measured by the Taber Method in the direction defined by the longitudinal axis is in a range of 0.015 to 0.1 N cm.

In the case of the breast milk absorbent pad according to the present invention, both breasts of the wearer can be covered with a single pad and at least one of the upper and lower edges of the third section covering the chest region defined between the breasts is concavely curved toward the transverse axis of the breast milk absorbent pad so that the breasts can be position-stabilized within the pad even when the wearer moves her body.

The preferred embodiments of the present invention provide significant effects as will be described below.

According to the embodiment wherein the upper and lower edges in at least one of the first and second sections are provided with elastically stretchable/contractible members extending in the direction defined by the transverse axis and attached under tension to these upper and lower edges, the first section and/or the second section present(s) the three-dimensional dome-like shape(s) adapted to the shape(s) of the breast(s). Thus the breast(s) can fit the first section and/or the second section and can be reliably position-stabilized even if the wearer briskly moves her body or changes her posture. In this way, there is no possibility that any amount of breast milk might leak due to displacement of the breasts relative to the pad.

The concavely curved edge of the third section may preferably describe circular curve having no angular corner to assure that the wearer experiences no feeling of incompatibility even when the coupler means of the brassiere causes the edge of the third section to be compressed against the wearer's skin.

The elastically stretchable/contractible members are attached to the body fluid leak-barrier outer sheet facing away from the wearer's skin and therefore the contractile force of the elastically stretchable/contractible members are not directly exerted on the wearer's skin. Consequentially, it is not apprehended that the contractile force might cause the wearer to experience feeling of incompatibility and/or leave pressure marks on the wearer's skin.

According to the embodiment wherein the edge of the body fluid absorbent panel lying in the vicinity of the concavely curved edge of the third section does not intersect with the transverse axis, any amount of breast milk flowing down can be reliably absorbed by the underlying body fluid absorbent panel in the third section when the wearer breast-feeds her baby in side lying position.

According to the embodiment wherein the elastically stretchable/contractible member continuously extends along the linear edge, not only the first and second sections but also the third section can be kept in close contact with the wearer's skin under the contractile force of the elastically stretchable/contractible member so as to prevent reliably any amount of breast milk from leaking along the chest region defined between the breasts.

Dimension of the body fluid absorbent panel in the third section as measured in the direction defined by the longitudinal axis may be adjusted to the range of 0.4 to 0.8 times the dimension of the body fluid absorbent panel in the first and second sections as measured in the direction defined by the longitudinal axis to assure that the edges concavely curved inward in the third section function as the barriers against the upper breast (i.e., unused breast in the case of breast-feeding by the wearer in side lying position) otherwise tending to droop and any amount of breast milk flowing down is reliably absorbed in the third section.

Stiffness of the body fluid absorbent panel as measured by Taber Method in the direction defined by the longitudinal axis may be adjusted to the range of 0.015 to 0.1 N cm to assure that the first and second section present the dome-like shapes adapted to the shapes of the respective breasts under a contractile force of the elastically stretchable/contractible members and the third section is deformed under a compressive force of the coupler means of the brassiere so as to come in close contact with the wearer's skin. In this way, anxiety that any amount of breast milk might leak sideways can be effectively prevented.

DETAILED DESCRIPTION OF THE PREFERRED EMBODIMENTS

Details of a breast milk absorbent pad according to the present invention will be more fully understood from the description given hereunder with reference to the accompanying drawings.

Figure 1:
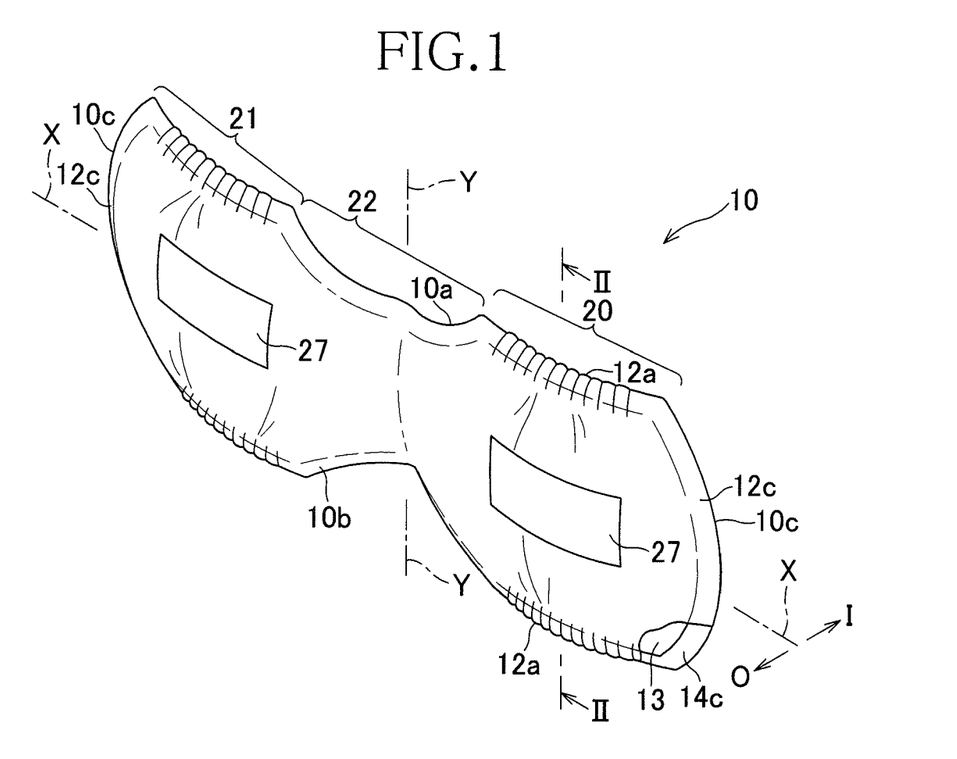
FIG. 1 is a partially cutaway perspective view of a breast milk absorbent pad as viewed from the outer surface thereof facing away from the wearer's skin.
Figure 2:
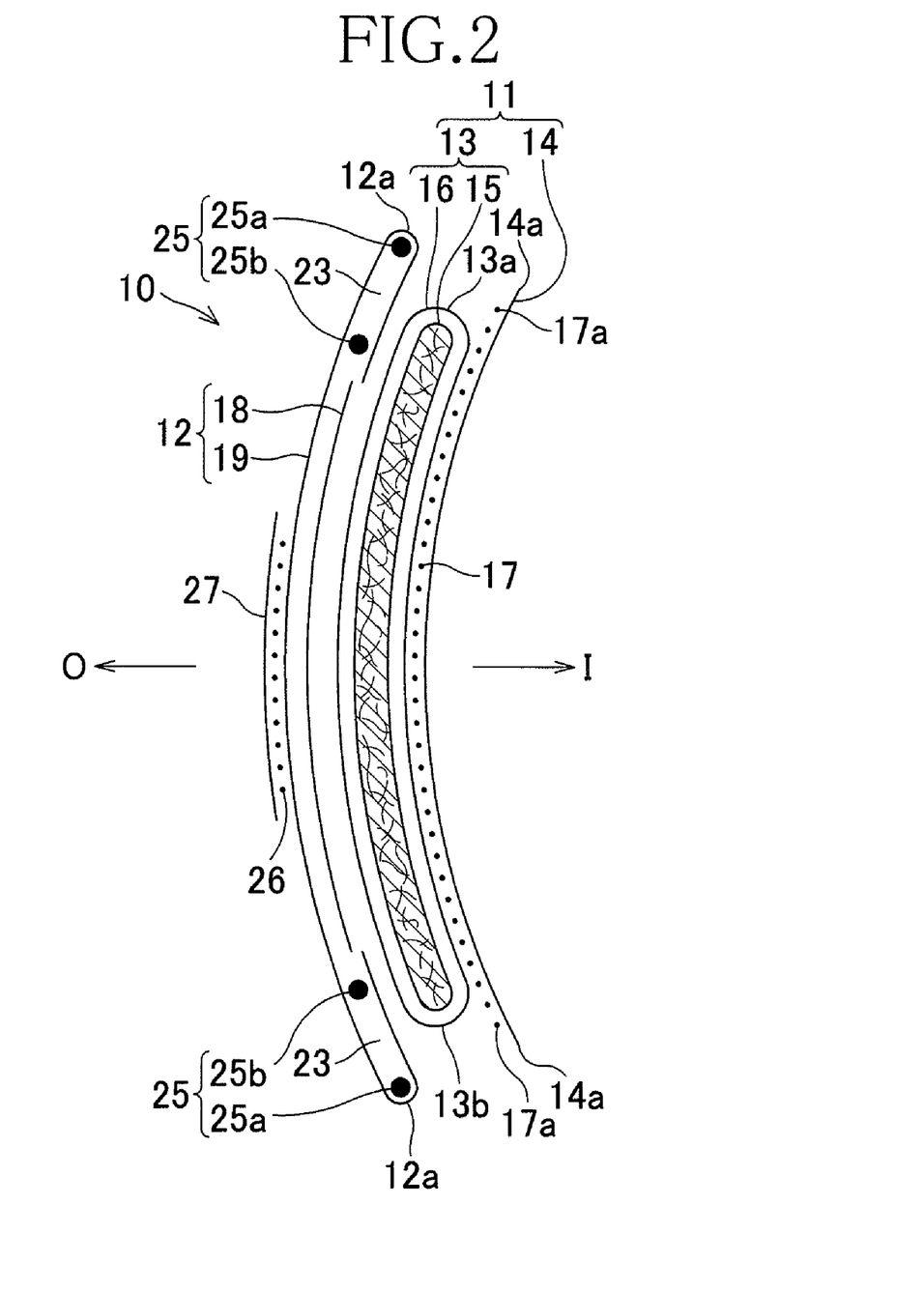
FIG. 2 is a schematic sectional view taken along the line II-II in FIG. 1.

FIG. 1 is a partially cutaway perspective view of a breast milk absorbent pad as viewed from the outer surface thereof facing away from the wearer's skin and FIG. 2 is a schematic sectional view taken along a line II-II in FIG. 1. As will be apparent from FIGS. 1 and 2, the breast milk absorbent pad 10 is generally defined by a longitudinal axis Y, a transverse axis X, an inner side I facing the wearer's skin and an outer side O facing away from the wearer's skin and comprises a body fluid absorbent layer 11 and a body fluid leak-barrier outer sheet 12. The breast milk absorbent pad is divided into first and second sections 20, 21 adapted to cover respective breasts and a third section 22 integrally extending between these first and second sections 20, 21. The breast milk absorbent pad 10 is configured in plane symmetry about the longitudinal axis Y so as to be substantially hourglass-shaped as a whole (See FIG. 3).

The body fluid absorbent layer 11 comprises a body fluid absorbent panel 13 and a body fluid pervious inner sheet 14 adapted to cover the inner side I facing the wearer's skin. The body fluid absorbent panel 13 comprises a body fluid absorbent core 15 completely wrapped with body fluid spreadable shape retaining sheet 16.

The body fluid absorbent core 15 comprises fluff pulp as base material mixed with super-absorbent polymer particles so as to present a panel-like shape and the shape retaining sheet 16 such as tissue paper. The shape retaining sheet 16 is intermittently coated with hot melt adhesive (not shown) by means of which the shape retaining sheet 16 is stabilized to wrap the body fluid absorbent core 15. In this way, the shape retaining sheet 16 is able not only to retain a desired shape of the body fluid absorbent core 15 but also to eliminate a possibility that the constituent material of the body fluid absorbent core 15, particularly, the polymer particles might fall off from the core 15.

The inner sheet 14 defining the inner side I facing the wearer's skin may be formed by thermoplastic synthetic fibrous nonwoven fabric or perforated plastic film, more preferably by fibrous nonwoven fabric such as spun bonded or air-through nonwoven fabric in any case having a basis weight preferably in a range of 10 to 40 g/m². The inner sheet 14 is intermittently coated with hot melt adhesive 17 by means of which the inner sheet 14 is stabilized to cover the body fluid absorbent panel 13. It is possible to form the inner sheet 14 from two or more layers of such fibrous nonwoven fabric and/or the perforated plastic film. Upper and lower edges 14a of the inner sheet 14 as well as upper and lower edges 17a of the region coated with hot melt adhesive 17 extend beyond upper and lower edges 13a, 13b of the body fluid absorbent panel 13 in a direction defined by the longitudinal axis Y.

The outer sheet 12 defining the outer side O facing away from the wearer's skin may be formed by plastic film 18 having a basis weight preferably in a range of 10 to 40 g/m² and fibrous nonwoven fabric 19 made of thermoplastic synthetic fiber or preferably laminated fibrous nonwoven fabric such as spun bonded/melt blown/spun bonded (SMS) laminate fibrous nonwoven fabric having a basis weight preferably in a range of 10 to 40 g/m². The plastic film 18 and the fibrous nonwoven fabric 19 of thermoplastic synthetic fiber are bonded together by means of hot melt adhesive (not shown) along a periphery of the plastic film 18.

The breast milk absorbent pad 10 having the outer surface formed by the fibrous nonwoven fabric 19 as has been described above is free from an anxiety of slippage of the breast milk absorbent pad 10 with respect to the clothes because the fibrous nonwoven fabric 19 assures a high frictional contact with the clothes such as brassiere in comparison with the case in which the outer surface is defined by the plastic film 18. In addition, no excessive bonding effect is required in order to prevent such slippage of the pad 10 and therefore an area to be bonded as well as an amount of adhesive to be applied can be correspondingly reduced.

The upper and lower edges of the fibrous nonwoven fabric 19 are folded back onto the inner side of the breast milk absorbent pad 10 to form sleeves 23. Respective edges of these sleeves 23 extend beyond the upper and lower edges of the body fluid absorbent panel 13 in the direction defined by the longitudinal axis Y by the same dimensions of the upper and lower edges 14a of the inner sheet 14, respectively. It should be noted here that an alternative construction is also possible in which the outer sheet 12 comprises the plastic film 18 and the fibrous nonwoven fabric 19 laminated on the outer surface thereof without forming the sleeves 23. In this alternative construction, elastically stretchable/contractible members as will be described later will be sandwiched between these film 18 and fibrous nonwoven fabric 19.

The breast milk absorbent pad 10 has upper and lower flaps (referred to hereinafter as upper and lower edges) 10a, 10b and right and left flaps (referred to hereinafter as transversely opposite ends) 10c, 10c defined by respective portions of the outer sheet 12 and the inner sheet 14 extending outward beyond the outer periphery of the body fluid absorbent panel 13 (See FIG. 1). More specifically, the upper and lower edges 10a, 10b are defined by the upper and lower edges 12a and the upper and lower edges 14a of the inner sheet 14 while the transversely opposite ends 10c, 10c are defined by the opposite ends 12c of the outer sheet 12 and the opposite ends 14c of the inner sheet 14.

The upper and lower edges 12a, 14a extend outward beyond the upper and lower edges 13a of the body fluid absorbent panel 13 in the direction defined by the longitudinal axis Y and these edges 12a, 14a are bonded together by means of respective distal regions of adhesive 17 located slightly aside toward the transverse axis X.

Within the upper and lower sleeves 23 in the first and second sections 20, 21, first and second pairs of elastically stretchable/contractible members 25a, 25b each having a tensile force preferably in a range of 115 to 500 mN are respectively spaced from each other by a predetermined dimension in the direction defined by the longitudinal axis Y so as to extend in the direction defined by the transverse axis X and fixed under tension to the respective sleeves 23 by means of hot melt adhesive (not shown). Specifically, the first pair of elastically stretchable/contractible members 25a extend in the direction defined by the transverse axis X along the upper and lower edges of the respective sleeves 23 while the second pair of elastically stretchable/contractible members 25b extend in the direction defined by the transverse direction X on the outer side O facing away from the wearer's skin along the upper and lower edges 13a, 13b of the body fluid absorbent panel 13 which are spaced inward from and in parallel to the first pair of elastically stretchable/contractible members 25a. Contractible force of the first pair of elastically stretchable/contractible members 25a functions to maintain the upper and lower edges 10a, 10b of the first and second sections 20, 21 in close contact with the wearer's skin while contractible force of the second pair of elastically stretchable/contractible members 25b functions to bow the body fluid absorbent panel 13 having high stiffness compared to the outer sheet 12 and the inner sheet 14 having a high flexibility in the first and second sections 20, 21, together with these sheets 12, 14 so that the inner side I facing the wearer's skin may present a concave shape. As a result, the first and second sections 20, 21 present dome-like shapes adapted to the shapes of the respective breasts.

The elastically stretchable/contractible members 25 attached to the upper and lower edges 12a of the outer sheet 12 ensures that no stretch stress of the elastically stretchable/contractible members 25 is directly transmitted to the upper and lower edges 14a of the inner sheet 14 kept in direct contact with the wearer's skin. Consequentially, leaks of breast milk beyond the upper and lower edges 10a, 10b of the pad 10 can be reliably prevented without an apprehension that gathers might formed along the upper and lower edges 14a of the inner sheet 14 which would otherwise make the wearer experience feeling of incompatibility and/or leave pressure marks on the wearer's skin. It should be understood here that the elastically stretchable/contractible members 25 may be attached to the upper and lower edges 10a, 10b in at least one of the first and second sections 20, 21 so far as any effective countermeasure is devised to prevent the unused breast from drooping during breast-feeding in side lying position.

On the outer surface of the outer sheet 12 in the first and second sections 20, 21, anti-slippage pressure-sensitive adhesive 26 used to fix the breast milk absorbent pad 10 to the brasserie and/or clothes and a separators 27 covering this adhesive 26 extend in the direction defined by the transverse axis X. Such anti-slippage pressure-sensitive adhesive 26 provided on the first and second sections 20, 21 eliminates a possibility that the breast milk absorbent pad 10 might fall off from the brasserie or clothes even when any one of the first and second sections 20, 21 is released from the brasserie or the clothes for the purpose of breast-feeding.

Figure 3:
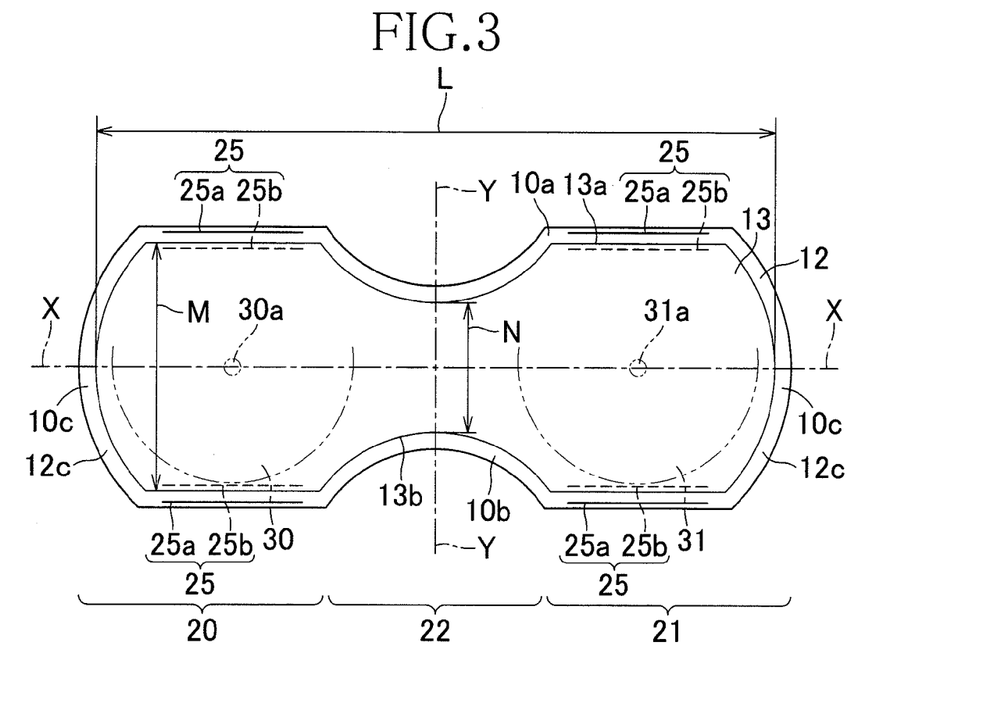
FIG. 3 is a plan view of the breast milk absorbent pad as viewed from the inner side thereof with portions removed for clarity.

FIG. 3 is a plan view showing the inner side of the breast milk absorbent pad 10 with the inner sheet 14 and the sleeves 23 removed.

As has previously been described, each of the first and second sections 20, 21 covering the respective breasts can take a three-dimensional shape adapted to the shape of the associated breast under the contractible force while the upper and lower edges 10a, 10b of the third section 22 is curved inward with respect to the breast milk absorbent pad 10, describing a circular arc so that the first and second sections 20, 21 may substantially fit the respective breasts. Consequentially, it is not apprehended that positions of the respective breasts 30, 31 might get out of desired association with the respective breasts due to significant movement as well as posture change of the wearer.

During a nursing period, mother sometimes lies still alongside her baby to breast-feed her baby for example when the baby cries him-or herself to sleep at bed time. In the course of such breast-feeding at the side lying position, breast milk is released also from a nipple of the breast being not used for feeding the baby due to one of inevitable physiological phenomena. In such situation, the breast milk absorbent pad of prior art comprising a pair of independent pads separated from each other so that the breasts are independently covered with these two pads has been disadvantageous in that the amount of breast milk released from the nipple of the breast unused for milk feeding may flow downward (i.e., toward the breast being used for milk feeding) and leak out along the chest region between the breasts. This problem has been solved by a breast milk absorbent pad 110 of prior art but improved as shown by FIG. 5. With this breast milk absorbent pad 110 of prior art, both breasts 130, 131 are reliably covered with the single pad 110 and it is not apprehended that the amount of breast milk flowing downward might leak out along the chest region defined between the breasts 130, 131. This breast milk absorbent pad 110 is provided in the chest region defined between the breasts 130, 131 with an absorbent pad. In other words, compared to the paired breast absorbent pads separated from each other, this improved pad 110 of prior art ensures the body fluid absorbent panel thereof to have a relatively large area and thereby to improve an absorption capacity for breast milk.

However, the breast milk absorbent pad 110 has a transversely longer elliptical shape adapted to cover both breasts and has no means in the chest region defined between the breasts to distinguish the respective breasts from each other. In other words, this pad has not three-dimensional shape adapted to the respective breasts. As a result, significant movement and/or posture change of the wearer may cause positions of the respective breasts 130, 131 to get out of proper positions vertically and/or laterally relative to the breast milk absorbent pad 110. When the breasts are out of desired positions (at which the nipples lie on or in the vicinity of the transverse axis X), the wearer experiences feeling of incompatibility and, in each case, the wearer is required to correct the positions of the respective breasts. Such correction takes a lot of trouble and bothersome for the wearer.

In the course of breast-feeding by the wearer in her recumbent position, the breasts necessarily droop under own weight thereof. However, the breast milk absorbent pad 110 itself does not droop together with the breasts since the pad 110 is affixed to the brassiere or clothes. Once the breasts have drooped within the pad 110, the nipples 131a are no more in contact with the inner surface of the pad 110 and consequentially there is a possibility that an amount of breast milk released from the nipples 131a might flow down along the wearer's skin and the wearer's clothes might be contaminated therewith.

In the case of the breast milk absorbent pad 10 according to the present invention, the first and second sections 20, 21 covering the respective breasts present, under the contractile force of the elastically stretchable/contractible member 25, the three-dimensional shapes adapted to the shapes of the breasts while the third section 22 facing the chest region defined between the breasts 30, 31 is concavely curved toward the transverse axis X. Such unique construction ensures the breasts 30, 31 to be stably held within the first and second sections 20, 21, respectively. Therefore, even when the wearer is in side lying position, the upper breast as viewed in this side lying position might droop as the pad of prior art has been the case. More specifically, in the course of breast-feeding with the one breast 30 by the wearer in side lying position, the other breast 31 is effectively protected by the upper and lower edges 10a, 10b of the third section 22 serving as barriers from drooping downward (i.e., toward the breast 30) across the third section 22. In addition, the nipple 31a of this unused breast 31 is well maintained in contact with the inner surface of the breast milk absorbent pad 10 and thereby it is ensured that an amount of breast milk released from this nipple 31a is rapidly and reliably absorbed by the third section 22 lying below.

In order that the breasts 30, 31 can be stably held at desired positions within the first and second sections 20, 21, respectively, it is essential that at least one of the upper and lower edges 10a, 10b of the third section 22 is concavely curved toward the transverse axis X. While a specific shape of the upper and/or lower edges 10a, 10b of the third section 22 concavely curved toward the transverse axis X may be circular or angular, the circular curve is rather preferable from the viewpoint that the circular curve has none of angular corners which might cause the wearer to experience feeling of incompatibility when the sides of the respective breasts 30, 31 facing the third section 22 come in contact with the curved upper and/or lower edges of the third section 22.

In order that the amount of breast milk released from the nipples 30a, 31a can be reliably absorbed by the third section 22, it is preferred that the upper and lower edges 10a, 10b of the third section 22 are spaced from the transverse axis X of the breast milk absorbent pad 10 by a predetermined dimension. This is for the reason as follows: With the breast milk absorbent pad put on the wearer, the respective nipples 30a, 31a of the breasts 30, 31 lie substantially on or in the vicinity of the transverse axis X of the pad 10 and, if the upper and lower edges 13a, 13b of the body fluid absorbent panel 13 in the third section 22 are concavely curved so as to intersect the transverse axis X, it is impossible, during breast-feeding by the wearer side lying, for the body fluid absorbent panel 13 in the third section 22 to reliably absorb the amount of breast milk flowing downward. Consequentially, there is anxiety that such amount of breast milk might leak out beyond the upper and lower edges 10a, 10b of the third section 22. While a dimension N of the body fluid absorbent panel 13 in the third section 22 in the direction defined by the transverse axis X may be appropriately varied depending on the size of the pad to avoid said inconveniences, if a dimension L of the body fluid absorbent panel 13 as measured in the direction defined by the transverse axis X is about 250 mm and a dimension M thereof in the first and second sections 20, 21 as measured in the direction defined by the longitudinal direction Y is about 100 mm, the dimension N of the body fluid absorbent panel 13 in the third section 22 as measured in the direction defined by the longitudinal axis Y is preferably in a range of 40 to 80 mm.

As has previously been described, both the first section 20 and the second section 21 present, under the contractile force of the elastically stretchable/contractible members 25, the three-dimensional shapes adapted to the shapes of the respective breasts and have the upper and lower edges 10a, 10b closely in contact with the wearer's skin. On the contrary, the third section 22 includes none of the elastically stretchable/contractible members 25 and is readily spaced from the wearer's skin. However, the breast milk absorbent pad may be interposed between the brassiere and the wearer's skin to ensure that a coupler section adapted to couple both cups of the brassiere functions to compress the third section 22 against the wearer's skin and thereby to keep the third section 22 in close contact with the wearer's skin. Even after the brasserie has been removed, the third section 22 is maintained in such close contact with the wearer's skin under its flexible shape retaining ability and able to absorb the amount of breast milk released from the nipples 30a, 31a. A stiffness of the body fluid absorbent panel 13 in the direction defined by the longitudinal axis Y to achieve such effect is preferably in a range of 0.015 to 0.1 N cm, more preferably in a range of 0.018 to 0.03 N cm as measured in accordance with Taber Method (JIS P8125). If the stiffness of the body fluid absorbent panel 13 is 0.015 N cm or less, the body fluid absorbent panel 13 will have a relatively high flexibility and excessively curved under the contractile force of the elastically stretchable/contractible members 25, making it difficult to take the desired three-dimensional shape adapted to the shape of the breast. If the stiffness of the body fluid absorbent panel 13 is 0.1 N cm or higher, on the contrary, the body fluid absorbent panel 13 will have a relatively high stiffness and a correspondingly high shape retaining ability. Due to such high shape retaining ability, it will be difficult for the body fluid absorbent panel 13 to be smoothly deformed to the desired three-dimensional shape adapted to the shape of the breast even under the contractile force of the elastically stretchable/contractible members 25. Also under the compressive force of the coupler means of the brasserie against the wearer's skin, the third section 22 will not be sufficiently deformed to fit the wearer's skin.

Figure 4:
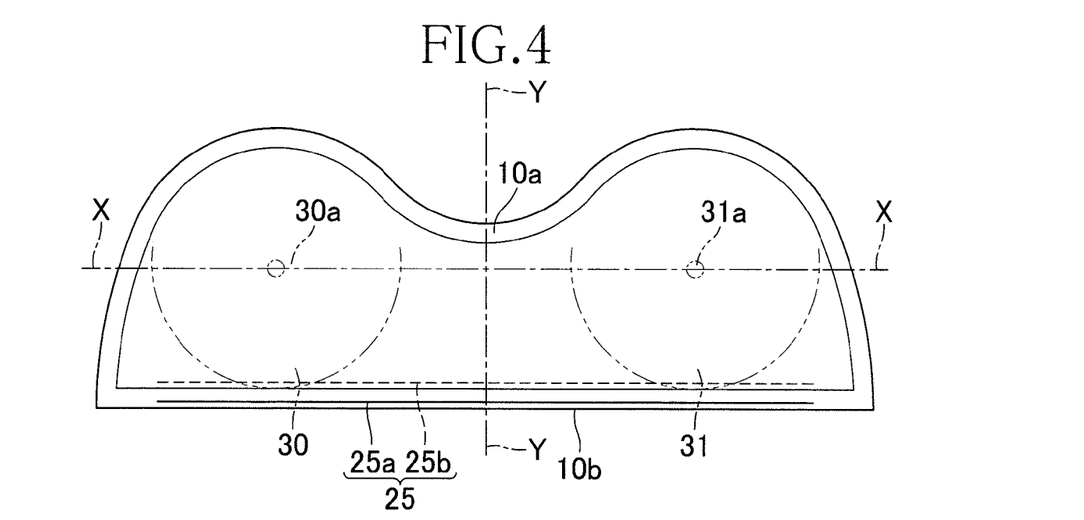
FIG. 4 is a view similar to FIG. 3, showing an alternative embodiment of the breast milk absorbent pad.

FIG. 4 is a plan view similar to FIG. 3, showing an alternative embodiment of the breast milk absorbent pad 10.

This alternative embodiment is basically similar to the embodiment shown by FIG. 3 in many features and, to avoid double description, only the features distinguished from the previously described embodiment will be described. The embodiment of FIG. 4 is distinguished from the embodiment of FIG. 3 in that the lower edge 10b of the breast milk absorbent pad 10 linearly extends in the direction defined by the transverse axis X while the upper edge 10b in the first and second sections 20, 21 is convexly curved upward in the direction defined by the longitudinal axis Y so as to describe circular arcs and the elastically stretchable/contractible member 25 continuously extends along the lower edge 10b of the first and second sections 20, 21. According to this embodiment, the upper edge 10a of the first and second sections 20, 21 describe circular arcs adapted to the outer shapes of the breasts. The elastically stretchable/contractible member 25 attached to the lower edge 10b ensures that upper and lower regions of the respective breasts fit within the first and second sections 20, 21, respectively, and there is no possibility that a change of the wearer's posture might cause the breasts 30, 31 to be out of the desired alignment with the associated first and second sections 20, 21. As far as stabilization of the breasts 30, 31 is concerned, an alternative construction is also possible, according to which the upper edge 10a is linear while the lower edge 10b describes the circular arcs. In this case, the elastically stretchable/contractible member 25 continuously extends along the upper edge 10a of the first and second sections 20, 21. Furthermore, in order to improve the stabilizing effect for the breasts 30, 31, the elastically stretchable/contractible members 25 may be attached not only to the linear edge but also to the edge of the first and second sections 20, 21 describing the circular arcs.

The entire disclosure of Japanese Patent application No. 2007-39809 filed on Feb. 20, 2007 including specification, drawings and abstract are herein incorporated by reference in its entirety.

What is claimed is:

1. A breast milk absorbent pad for releasable attachment to a brassiere or other clothing having a longitudinal axis, a transverse axis, an inner side adapted to face a pad wearer's skin, an outer side adapted to face away from the pad wearer's skin, and upper and lower edges opposed to each other in a direction defined by said longitudinal axis and extending in a direction defined by said transverse axis, said breast milk absorbent pad further comprising a body fluid leak-barrier outer sheet lying on said outer side adapted to face away from the pad wearer's skin, and a body fluid absorbent layer comprised of a body fluid pervious inner sheet lying on said inner side adapted to face the pad wearer's skin and a body fluid absorbent panel between said inner and outer sheets, wherein said breast milk absorbent pad further comprises a first section adapted to form a three-dimensional cup shape that is configured to cover only one breast of a pair of breasts, a second section adapted to form a three-dimensional cup shape that is configured to cover only the other breast of the pair of breasts, said first and second sections being symmetric about said longitudinal axis, and a third section extending continuously between said first and second sections adapted to be maintained in close contact with the wearer's skin between the pair of breasts when the first and second cup-shaped sections cover the pair of breasts, respectively, wherein:

the third section includes said upper and lower edge of said pad and at least one of said upper and lower edges in said third section of the breast milk absorbent pad is shaped to be concavely curved toward said transverse axis.

2. The breast milk absorbent pad as claimed in claim 1, wherein at least one of said first and second sections of the breast milk absorbent pad include said upper and lower edges and elastically stretchable/contractible members extending in said direction defined by said transverse axis and attached under tension to said upper and lower edges of said at least one of said first and second sections.

3. The breast milk absorbent pad as claimed in claim 2, wherein said upper and lower edges are defined by upper and lower flaps extending outward from upper and lower edges of said body fluid absorbent panel in said direction defined by said longitudinal axis, said upper and lower flaps are formed by edges of said inner sheet extending outward beyond said upper and lower edges of said body fluid absorbent panel and edges of said outer sheet extending outward beyond said upper and lower edges of said body fluid absorbent panel and wherein said elastically stretchable/contractible members comprise a first pair of elastically stretchable/contractible members attached under tension to said outer sheet adjacent said edges thereof and a second pair of elastically stretchable/contractible members attached under tension to said outer sheet adjacent said upper and lower edges of said body fluid absorbent panel.

4. The breast milk absorbent pad as claimed in claim 1, wherein said at least one of said upper and lower edges in said third section of the breast milk absorbent pad describes a circular arc.

5. The breast milk absorbent pad as claimed in claimed 1, wherein the other of the at least one of said upper and lower edges opposed to the at least one of the upper and lower edges concavely curved toward said transverse axis in said third section of the breast milk absorbent pad is linear and continuously extends along said first section, said third section and said second section of the breast milk absorbent pad, and said pad further comprising an elastically stretchable/contractible member continuously extending along said other edge of said first, third and second sections.

6. The breast milk absorbent pad as claimed in claim 1, wherein a stiffness of said body fluid absorbent panel as measured by the Taber Method in the direction defined by said longitudinal axis is in a range of 0.015 to 0.1 N cm.

7. The breast milk absorbent pad as claimed in claim 1, wherein the body fluid absorbent panel includes a first section, a second section and a third section defining respective first, second and third sections of said pad.

8. The breast milk absorbent pad as claimed in claim 7, wherein the other of the at least upper and lower edges in the third section is concavely curved toward said transverse axis and the third section of said body fluid absorbent panel having respective upper and lower edges that extend in a vicinity of said curved upper and lower edges of the pad that are concavely curved toward said transverse axis but do not intersect with said transverse axis.

9. The breast milk absorbent pad as claimed in claim 7, wherein a dimension of said body fluid absorbent panel in said third section of said breast milk absorbent pad as measured in the direction defined by said longitudinal axis is in a range of 0.4 to 0.8 times a dimension of said body fluid absorbent panel in said first and second sections of said breast milk absorbent pad as measured in the direction defined by said longitudinal direction.

\* \* \* \* \*